United States Patent [19]
Lisowsky

[11] Patent Number: 5,625,086
[45] Date of Patent: Apr. 29, 1997

[54] PROCESS FOR THE PREPARATION OF CYCLOPENTADIENYLTRIALKOXYTITANIUM DERIVATIVES

[75] Inventor: Richard Lisowsky, Kamen, Germany

[73] Assignee: Witco GmbH, Bergkamen, Germany

[21] Appl. No.: 674,496

[22] Filed: Jun. 26, 1996

[30] Foreign Application Priority Data

Jul. 12, 1995 [EP] European Pat. Off. ............... 95110905

[51] Int. Cl.$^6$ ............................... C07F 17/00; C07F 7/28
[52] U.S. Cl. .......................... 556/54; 526/943; 502/103; 502/152
[58] Field of Search ............................. 556/54; 526/943; 502/103, 152

[56] References Cited

FOREIGN PATENT DOCUMENTS

| | | |
|---|---|---|
| 0322663 | 7/1989 | European Pat. Off. . |
| 0559108 | 9/1993 | European Pat. Off. . |
| WO94/10216 | 5/1994 | WIPO . |

OTHER PUBLICATIONS

G. Llinas et al., "($C_5Me_5$)$SiMe_3$ as a mild and effective reagent for transfer of the $C_5Me_5$ ring: an improved route to monopentamethylcyclopentadienyl trihalides of the group 4 elements", 1988, *Journal of Organometallic Chemistry,* 340:37–40.

P.C. Wailes et al., *Organometallic Chemistry of Titanium, Circonium, and Hafnium,* 1974, 34–39.

R.B. King et al., "Organometallic Chemistry of the Transition Metals XXI. Some π-Pentamethylcyclopentadienyl Derivatives of Various Transition Metals", 1967, *J. Organometal. Chem.* 8:287–297.

H. Rohl, et al., "Pentamethyl–cyclopentadienyl–titantrichlorid", 1962, *Angew. Chem.,* p. 155.

A.N. Nesmeyanov, et al., "Reaction of cyclopentadienylsodium with alkoxytitanium chlorides", 1961, *Alicylic Compounds,* pp. 6397–6398.

A.N. Nesmeyanov, et al., "Mono–π–cyclopentadienyl derivatives of titanium", 1961, *Heterocyclic Compounds,* pp. 22273–22274.

Ulf Thewalt, "Titan–Organische Verbindungen", 1977, *Gmelin Handbuch der Anorganischen Chemie,* pp. 136–156.

*Primary Examiner*—Porfirio Nazario-Gonzalez
*Attorney, Agent, or Firm*—Scully, Scott, Murphy & Presser

[57] ABSTRACT

The invention relates to a process for the preparation of cyclopentadienyltrialkoxy derivatives of the general formula

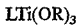

$LTi(OR)_3$ by reaction of cyclopentadienyltrialkoxy trihalide with alcohol in an inert solvent, which is characterized in that the reaction is performed in the presence of alkoxide.

4 Claims, No Drawings

PROCESS FOR THE PREPARATION OF CYCLOPENTADIENYLTRIALKOXYTITANIUM DERIVATIVES

FIELD OF THE INVENTION

The invention relates to a novel process for the preparation of cyclopentadienyltrialkoxytitanium derivatives by reaction of cyclopentadienyltrialkoxytitanium trichloride with alcohols in the presence of alkoxides.

BACKGROUND OF THE INVENTION

Cyclopentadienyltrialkoxytitanium compounds of the general formula $LTi(OR)_3$, in which L can be cyclopentadienyl radical and R can be an alkyl or aryl radical, are described in the literature as starting components for catalyst systems for the stereospecific polymerization of styrene: EP-A-322 663, EP-A-559 108, WO 94/10216.

Some processes for the preparation of titanium compounds of the formula $LTi(OR)_3$, are described in the literature.

According to Chemical Abstracts (CA): 55: 6398g; CA: 22273c; CA: 68: 13138e, di- or trialkoxytitanium chlorides are reacted in an inert solvent with metallated cyclopentadienyl derivatives according to the following general reaction scheme:

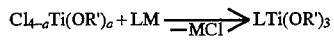

where L is a cyclopentadienyl derivative; M is Li, Na, or MgCl; R' is an alkyl or aryl radical; and a is 2 or 3.

This process has serious disadvantages, in that the compounds $Cl_{4-a}Ti(OR')_3$ have to be prepared in a complex manner from $TiCl_4$ and $Ti(OR^1)_4$ and purified.

According to Wailes, Coutts, Weigold: Organometallic Chemistry of Titanium, Zirconium and Hafnium, Academic Press, New York and London, pages 34–39, cyclopentadienyltitanium trichloride are reacted in inert solvents with alcohols in the presence of tertiary amine according to the general equation

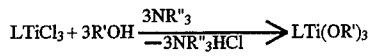

in which R" are alkyl radicals and L and R' have the meaning given above.

If the reaction is carried out under suitable conditions, although good yields of the desired reaction product can be achieved, the amine hydrochloride arising as a voluminous precipitate causes considerable problems in carrying out the reaction and in separation and workup.

Furthermore, despite considerable excesses of R'OH and base, complete replacement of the chlorine for the OR' radical can hardly be achieved, so that the reaction products contain undesirable residual chlorine contents.

One object of the present invention is therefore to provide an industrially elegant, cost-effective process by which very largely chloride-free, that is completely substituted, end products can be prepared without the formation of interfering voluminous precipitates.

BRIEF SUMMARY OF THE INVENTION

Surprisingly, it has now been found that this object can be achieved by reaction of cyclopentadienyltitanium trihalides with alcohols and their alkoxides in inert solvents. This is all the more surprising, since it is known that titanium compounds of this type have a tendency to eliminate the cyclopentadienyl group in the presence of alcohol.

The invention therefore relates to a process for the preparation of cyclopentadienytrialkoxy derivatives of the general formula

by reaction of cyclopentadienyltitanium trihalide with one or more alcohols in an inert solvent, in the presence of one or more alkoxides in accordance with the general equation

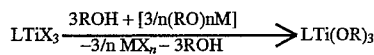

where
L is cyclopentadienyl of the formula

m is 1–5;
X is F, Cl, Br or I;
M is Li, Na, K, Mg or Ca;
each $R^1$ and R, independently of each other, is an unsubstituted or substituted alkyl or aryl radical containing 1 to 20 carbon atoms; and
n is the valency of the metal M.

Further subject-matter of the invention is characterized in that the compound $LTiX_3$ is reacted in an inert solvent with an alcohol/alkoxide mixture at a temperature of −78° C. to approximately 120° C., the salt that is formed and the solvent are removed, and the reaction product is optionally purified by conventional processes.

Further subject-matter is characterized in that a cyclopentadienyl radical L is used in which each $R^1$ is independently a methyl, ethyl or n-propyl radical and m is 3–5.

Further subject-matter is characterized in that R is a methyl, ethyl or n-propyl radical.

DETAILED DESCRIPTION OF THE INVENTION

The titanium compounds of the formula $LTiX_3$ which are used for the process of the invention and in which L denotes an unsubstituted or substituted cyclopentadienyl radical and X is F, Cl, Br or I can be prepared in accordance with processes disclosed in the literature: J. Organomental. Chem 1967, Vol. 8, p 287 ff; Angew. Chem. 1962, 74 page 155 ff; J. Organomental. Chem. 1988, 340, p. 37 ff; Gmelin Handbook der Anorganischen chemie, Titan-Organische Verbindungen [Gmelin's Handbook of Inorganic Chemistry, Organotitanium Compounds], Volume 40, Part 1, pages 136–156, Springer-Verlag, Berlin-Heidelberg-New York (1977).

Compounds preferred according to the invention are trisubstituted and higher substituted, in particular trimethyl, tetramethyl and pentamethyl compounds, in which chloride is preferred as halide.

Suitable alcohols used conjointly according to the invention are the commercial products, in particular aliphatic, unbranched or branched monofunctional alcohols having 1–10 carbon atoms such as, preferably, methanol, ethanol, n-propanol, and unsubstituted or substituted aromatic alcohols having 6–18 carbon atoms such as, preferably, phenol.

If necessary, these alcohols are dried by conventional processes.

The alkoxides $(RO)_nM$ can be prepared by known processes by reaction of the corresponding metal—preferably Li, Na, K, Mg or Ca—or are obtainable as commercial industrial products.

The alcohol ROH and the alkoxide RO⁻ are used in at least stoichiometric amounts, based on the halide to be replaced in the compound $LTiX_3$. If necessary, excesses of alcohol can be used in order to improve the ease of dispensing of the alcohol/alkoxide mixture. The excess is restricted to the optimum necessary for dispensing.

The cyclopentadienyl trihalide is preferably reacted according to the invention with the alcohol/alkoxide mixture in such a way that the compound $LTiX_3$ is first introduced in an inert solvent, such as, preferably, in aromatic hydrocarbons, in particular toluene, or xylene, aliphatic hydrocarbons such as, in particular, tetrahydrofuran, tert-butyl methyl ether, or diethyl ether; or special inert halogenated hydrocarbons such as, in particular, methylene chloride. The amount of inert solvent is not critical. It is kept as small as possible for reasons of reaction technique. Selection criteria are, in particular, stirrability of the reaction mixture and ease of separation of the salt formed.

Into this mixture is dispensed the alcohol/alkoxide mixture under inert conditions (protective gas).

The reaction temperature during dispensing is preferably kept between approximately −78° C. and approximately 25° C. and subsequently increased, if appropriate steplessly, up to the reflux temperature of the mixture. The reaction time after dispensing, depending on the temperature chosen, is between 0.5 and 2 hours; generally, 2 hours at the reflux temperature of the mixture are sufficient.

After the reaction is complete, the precipitated salt $MX_n$ which forms is separated off, the solvent is removed and the reaction product, if desired, is purified by conventional processes such as fractional distillation or recrystallization.

EXAMPLES

Example 1

80 g of 1, 2, 3, 4, 5-pentamethylcyclopentadienyl-titanium trichloride (0.267 mol) was first introduced in 300 ml of toluene under an $N_2$ atmosphere, cooled to −10° C. and a solution of 43.3 g of sodium methoxide in methanol, freshly prepared by conventional methods from 18.4 g of Na (0.8 mol) and 200 ml of methanol, was added dropwise. After addition was complete, the reaction was continued for a further 2 hours at room temperature and 2 hours under reflux. After cooling to room temperature, the precipitated NaCl was filtered off, the toluene and methanol were distilled off under reduced pressure and the remaining crude product was subjected to fractional distillation.

The fraction of 1 2, 3, 4, 5-pentamethylcyclopentadienyl-trimethoxytitanium produced at 108°–100° C. and 6 mbar gave a yield of 58 g=79% of theory and the following analytical values:

¹H-NMR: (CDCl₃) 4.04 ppm (s, 9 H, MeO); 2.02 ppm (s, 15 H, Me₅Cp) Ti: (calculated; 17.3%) founded: 17.2% Ci: <0.001%

Example 2

The process according to Example 1 was repeated with the change that, instead of the freshly prepared methoxide 144 g (0.8 mol) of a commercial industrial product from BASF, obtainable as "sodium methoxide, 30% strength in methanol" was used.

60.5 g (=82% of theory) of pure 1, 2, 3, 4, 5-pentamethylcyclopentadienyltrimethoxytitanium having the following analytical values was obtained:

¹H-NMR: identical to that in Example 1 Ti: (calculated: 17.3%) found: 17.3% Ci: <0.001%

Example 3

Following the procedure of Example 2, 55.1 g (0.2 mol ) of 1, 2, 3, 4-tetramethylcyclopentadienyltitanium trichloride was first introduced in 250 ml of toluene and 108 g (0.6 mol) of 30% strength commercial (BASF) methoxide was added dropwise at −10° C.

After addition was completed, the reaction was carried out for a further 1 hour at room temperature and 2 hours under reflux.

After removal of the NaCl and distillation, 40.9 g (0.156 mol; 79% of theory) of tetramethylcyclopentadienyltrimethoxytitanium having the following analytical data were obtained:

¹H-NMR: (CDCl₃) 5.78 ppm (s, 1, h, h-Cp); 4.07 ppm (s, 9, H, Me-O); 2.08 ppm (s, 6 H, Me₂Cp); 2.00 ppm (s, 6 H, Me₂Cp).

Comparison Example 10 g of 1, 2, 3, 4, 5-pentamethylcyclopentadienyltrimethoxytitanium trichloride (34.5 mmol) was first introduced in 200 ml of toluene and a mixture of 4 g of methanol (125 mmol) and 12.7 of triethylamine (125 mmol) was added dropwise at room temperature.

After addition of ⅔ of the mixture, a further 100 ml of toluene had to be added to the reaction mixture, since stirring was no longer possible owing to the voluminous precipitation of triethylamine hydrochloride. After addition was completed, the mixture was further stirred for 4 hours. The triethylamine hydrochloride was then filtered off.

The filtercake had to be washed three times, each time with 80 ml of toluene, so that the product could be washed out for the most part.

The combined filtrates were then freed from toluene and the residue was distilled.

6.4 g of product (67% of theory) having the following analytical values was isolated:

¹H-NMR (CDCl₃) 4.04 (s, 9H, MeO); 2.02 (s, 15 H, Me₅Cp) Ti: (calculated: 17.3%) found: 17.1% Ci: 0.4%

What is claimed is:

1. A process for the preparation of a cyclopentadienytrialkoxy derivative of the general formula

by reacting cyclopentadienyltitanium trihalide in an inert solvent, with one or more alcohols in the presence of one or more alkoxides in accordance with the general equation

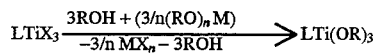

wherein

L is substituted cyclopentadienyl of the formula

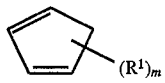

wherein m=1–5;

X is F, Cl, Br or I;

M is Li, Na, K, Mg, or Ca;

each $R^1$ and R group is independently of each other unsubstituted or substituted an alkyl or aryl radical containing 1 to 20 carbon atoms; and n is the valency of the metal M.

2. A process according to claim 1, wherein the compound $LTiX_3$ is reacted in an inert solvent with an alcohol/alkoxide mixture at a temperature of −78° C. to approximately 120° C., whereby a salt byproduct is formed; the salt formed and solvent are removed; and the reaction product is optionally purified.

3. A process according to claim 1, wherein a cyclopentadienyl radical L is used in which each $R^1$ is independently methyl, ethyl or n-propyl radical and m is 3–5.

4. A process according to claim 1, wherein R is a methyl, ethyl or n-propyl radical.

* * * * *